United States Patent [19]

Nabulon et al.

[11] Patent Number: 5,351,374
[45] Date of Patent: Oct. 4, 1994

[54] METHOD AND AN APPARATUS FOR THE CONTINUOUS CRIMPING OF THERMOPLASTIC THREADS

[76] Inventors: Werner Nabulon, Schneihalde 116, CH-8455 Rudlingen; Jorg Maier, Moosweg 23, CH-8500 Frauenfeld; Peter Grossenbacher, Tosstalstrasse 99, CH-8400 Winterthur; Felix Graf, Wylandstrasse 12, CH-8400 Winterthur; Armin Wirz, Im Grund, CH-8475 Ossingen, all of Switzerland

[21] Appl. No.: 13,716

[22] Filed: Feb. 4, 1993

[30] Foreign Application Priority Data

Feb. 7, 1992 [CH] Switzerland ............... 359/92
Jun. 3, 1992 [CH] Switzerland ............. 2052/92

[51] Int. Cl.$^5$ .................... D02G 1/12; G01N 33/36
[52] U.S. Cl. ......................... 28/271; 28/248; 28/250; 73/37.7; 364/470; 364/510
[58] Field of Search ............. 73/37, 37.5, 37.6, 37.7; 364/470, 510; 28/255, 256, 250, 248, 251, 263, 265, 271

[56] References Cited

U.S. PATENT DOCUMENTS

| | | | |
|---|---|---|---|
| 2,634,596 | 4/1953 | Pendleton et al. | 28/250 X |
| 3,037,260 | 6/1962 | Pike, Jr. | 28/248 X |
| 3,526,023 | 9/1970 | Mertens | 28/248 |
| 3,850,025 | 11/1974 | Reufer et al. | 73/37.7 |
| 4,067,092 | 1/1978 | Roberts . | |
| 4,162,564 | 7/1979 | Stanley | 28/248 |
| 4,184,361 | 1/1980 | Erben | 73/37.7 |
| 4,188,691 | 2/1980 | Matsumoto et al. | 28/255 |
| 4,462,143 | 7/1984 | Oswald et al. | 28/251 X |
| 4,547,934 | 10/1985 | Ford | 28/250 X |
| 4,720,807 | 1/1988 | Ferran et al. | 364/510 X |
| 4,782,566 | 3/1987 | Napnelone | 28/255 |
| 4,866,822 | 9/1989 | Keedy, Jr. et al. | 28/250 |
| 5,088,168 | 5/1991 | Berger | 28/249 |

FOREIGN PATENT DOCUMENTS

| | | | |
|---|---|---|---|
| 214159 | 10/1984 | German Democratic Rep. | 28/250 |
| 4000104 | 2/1989 | Japan | 28/250 |
| 918351 | 4/1982 | U.S.S.R. | 28/248 |
| 1382634 | 2/1975 | United Kingdom | 28/251 |

OTHER PUBLICATIONS

Fibre M.: Non-Isothermal Texturing at High Speed, Textile Institute and Industry, Jun. 1975; pp. 172-173: Foster.

*Primary Examiner*—Clifford D. Crowder
*Assistant Examiner*—John J. Calvert
*Attorney, Agent, or Firm*—Francis C. Hand

[57] ABSTRACT

Threads made from thermoplastic materials are textured, in that they are heated by a delivery medium in a delivery channel and conveyed through an orifice into a stuffer box where they are stuffed to form a plug. In order to maintain plug formation constant, the orifice area is monitored in a sensory manner and the measured signals are used for monitoring purposes as a measured quantity in a control loop, in which the supply of damming back medium, the conveying away speed of the plug, the position of the stuffer box walls, or the supply of delivery medium are used as manipulated variables. The measuring signals produced by monitoring can be compared with thresholds to produce control signals corresponding to the comparison result for activating alarm, warning or stopping elements. Sensory monitoring is carried out by measuring the dynamic pressure prevailing in the delivery channel close to the orifice, by measuring the dynamic pressure in a fluidic nozzle issuing into the stuffer box, or by monitoring with an optical sensor the interior of the stuffer box.

24 Claims, 4 Drawing Sheets

METHOD AND AN APPARATUS FOR THE CONTINUOUS CRIMPING OF THERMOPLASTIC THREADS

This invention relates to a method and an apparatus for the continuous crimping of thermoplastic threads. More particularly, this invention relates to a method and apparatus for monitoring the continuous crimping of thermoplastic threads.

As is known, various types of techniques have been employed for the continuous crimping of threads (fibril bundles) of thermoplastic material. For example, in some cases, the threads have been moved through a delivery channel with the aid of a hot delivery medium flowing under pressure, heated and then delivered through an orifice into a stuffer box. Generally, the stuffer box has been designed in such a way that the delivery medium is depressurized on passing out of the orifice. Upon travel in the stuffer box, the thread strikes a plug formed by the thread which has previously passed out of the orifice and crimping then takes place. The plug is then conveyed on at a speed which is lower than the thread speed in the delivery channel, cooled and then loosened to form a textured yarn.

The stuffer box in which the plug is formed can be bounded by stationary perforated walls, which longitudinally surround the plug and which e.g. comprise lamellas. The plug is pushed through the stuffer box by the dynamic pressure of the delivery medium against the friction on the stuffer box walls and leaves the stuffer box through a plug opening opposite to the orifice of the delivery channel. The stuffer box can also be provided with a delivery roller pair for discharging the plug in metered form.

The stuffer box can also be bounded only partly by stationary walls and partly by walls which move at the plug speed. A method and an apparatus for the continuous crimping of thermoplastic threads with a stuffer box, which in part has walls moving with the plug, is e.g. described in European patent 310 890. The described apparatus has a texturing nozzle with a delivery channel, an orifice and two shaped parts extending therefrom in the thread running direction and which form the stationary wall parts of the stuffer box. For the further conveying of the plug formed between the shaped parts, a channel formed by lateral guidance means is provided which passes around the circumference of a rotating plug delivery roller and into which extend the shaped parts. The Lateral guidance means of the channel constitute the stuffer box wall parts which move with the plug in the vicinity of the orifice. The plug passes from the stuffer box, between the lateral guidance means and around part of the circumference of the plug delivery roller and is then transferred to a further delivery member, where the plug is cooled and finally loosened to form a textured yarn.

The plug in the stuffer box is usually initiated following the introduction of the thread at the start of production by a temporary braking force, e.g. an air jet directed against the thread. During operation, an equilibrium exists between the dynamic pressure of the delivery medium pushing the plug and the frictional forces on the stuffer box walls braking the plug. This leads to a continuous plug formation and to a constant plug speed in the stuffer box.

The quality of the textured yarn is closely dependent on the uniformity of the crimping, i.e. the uniformity of plug formation. If the plug is missing, the yarn is not crimped. If plug formation starts too far from the orifice of the delivery channel, the plug is less dense, so that crimping is inadequate and is not sufficiently permanent. This means that for a high yarn quality, the position, consistency and speed of the plug must be kept as constant as possible.

In all known apparatuses for crimping thermoplastic material threads with the aid of a texturing nozzle and a stuffer box, irregularities can occur in plug formation. In particular, there can be situations where plug formation takes place too far from the orifice of the delivery channel or in fact no plug is formed, i.e. so-called blow outs. As a function of the apparatus, the blow outs are either temporary, i.e. they re-form without having any effect, or are permanent, i.e. the machine must be stopped in order to again obtain a regular plug formation.

As the faults in plug formation with the methods and apparatuses according to the prior art can only be discovered visually and are consequently often discovered too late, it is possible for textured yarn bobbins to have faults, which are due to undiscovered, temporary blow outs and which are only detected on the product produced from the yarn. Large reject quantities can be caused by permanent blow outs which are only discovered after a certain period of time.

Accordingly, it is an object of the invention to avoid any loss of yarn quality and production due to wastage caused by unstable plug formation and, in particular, blow outs during the crimping of thermoplastic threads.

It is another object of the invention to improve the quality of crimped thermoplastic yarns.

It is another object of the invention to provide a relatively simple technique for monitoring the crimping of thermoplastic yarns.

Briefly, the invention provides a method and apparatus for the continuous crimping of a thermoplastic thread. In particular, the invention provides a method and apparatus for monitoring the continuous crimping of a thermoplastic thread.

The method includes the steps of conveying a traveling length of thermoplastic thread at a predetermined thread speed through a delivery channel having a orifice at one end into a stuffer box, passing a heated flow of delivery medium into the channel for passage out of the orifice, braking the speed of the thread in the stuffer box to form a thread plug, and conveying the thread plug from the stuffer box at a plug speed less than the thread speed. In accordance with the invention, at least one characteristic of plug formation is monitored in the vicinity of the orifice of the delivery channel in a sensory manner in order to emit a signal corresponding to a measured value of the characteristic of plug formation.

In further regard with the method, the signal is processed to selectively maintain plug formation constant and/or to activate an alarm indicative of the characteristic of plug formation deviating from a preset value.

In accordance with the invention, the characteristic of plug function which is monitored may be the static pressure in the delivery channel adjacent the orifice. In another embodiment, the characteristic may be the pressure in the stuffer box adjacent to the orifice of the delivery channel. In still another embodiment, the characteristic may be the optical appearance of the thread plug in the stuffer box at a predetermined location.

Also, in accordance with the method, the processed signal which is produced may be used to control the discharge of the plug from the stuffer box by varying the exit speed of the plug. In another embodiment, the processed signal can be used to vary the quantity of a flowable medium fed into the stuffer box for braking the thread therein. In still another embodiment, the processed signal can be used to adjust a wall part of a stuffer box in order to vary the cross-section of a passage through the stuffer box. In still another embodiment, the processed signal can be used to vary the quantity of the delivery medium passed into the delivery channel. In any of the embodiments, the method may employ a step of establishing a threshold value for the processed signal so that an alarm can be activated in response to the threshold value being passed. Alternatively, conveyance of the thread in the delivery channel may be interrupted in response to the threshold value being passed.

The apparatus employs a texturing nozzle and a stuffer box of generally known construction, for example, as described in Swiss Patent Application 00359/92-0. For example, the texturing nozzle has a delivery channel for conveying a traveling length of thermoplastic thread at a predetermined thread speed, an inlet into the channel for a flowable delivery medium and an orifice at one end of the channel while the stuffer box is constructed to receive a thread from the orifice for forming a thread plug therein. In accordance with the invention, the apparatus includes a sensory means for monitoring at least one characteristic of plug formation as described above.

The sensory means may include a static pressure measuring element for measuring the pressure in the channel of a texturing nozzle adjacent to the orifice and emitting a signal in response thereto. In other embodiments, the sensory means may include an optical sensor in the stuffer box and/or a fluidic nozzle in the stuffer box adjacent to the orifice for a flow of air therethrough and a pressure measuring element for measuring the pressure in the nozzle in order to emit a signal corresponding thereto.

The invention is based on a continuous, automatic check or inspection of the plug formation, which is utilized for regulating or alarm purposes. This takes place by sensory monitoring of the area of the orifice, e.g. by measuring the static pressure or a quantity correlated with the static pressure in the delivery channel close to the orifice or immediately outside the orifice, or by optically monitoring the stuffer box close to the orifice and by further processing the signals obtained by sensory monitoring for regulating, control and/or alarm purposes.

The static pressure in the delivery channel is the difference between the total pressure, which is substantially constant, and the dynamic pressure, which is proportional to the square of the flow rate. In the case of an empty delivery channel (without thread) through which the delivery medium can flow unimpeded by any thread, the static pressure is at the lowest level, because the flow rate is high. If the medium conveys a thread through the delivery channel, then compared with the stationary pressure in the thread-free channel, the stationary pressure is higher, because the medium is dammed back at the thread. If a plug is formed upstream of the orifice in the stuffer box, the medium is dammed back to an even greater extent and the static pressure is correspondingly higher. Therefore, the nearer the orifice plug formation commences, the higher the static pressure. The measurement of the static pressure in the delivery channel close to the orifice can therefore be evaluated directly as an indication of the plug formation state. Much the same applies for the static pressure in the stuffer box, immediately outside the orifice.

In the same way, it is possible to monitor plug formation by optical sensors in the stuffer box. For good crimping, plug formation must commence close to the orifice of the delivery channel, but at the most at a predetermined, empirically determined distance therefrom. If plug formation starts too far away from the orifice, a blow out occurs. A blow out can be detected by an optical sensor, which monitors the stuffer box in areas of maximum acceptable spacing of the plug from the orifice.

As plug formation is dependent on the braking in the stuffer box and the further conveying of the plug, plug formation can be kept constant by regulating these quantities. The monitoring of plug formation and, in particular, the pressure in the vicinity of the orifice, can be carried out by means of a measuring element integrated into a control loop with a proportional/integral controller, whose control elements influence the braking action of the stuffer box wall and/or the conveying on, particularly the conveying on speed of the plug.

These and other objects and advantages of the invention will become more apparent from the following detailed description taken in conjunction with the accompanying drawings wherein:

FIG. 1 schematically illustrates an apparatus according to the invention;

FIG. 2 graphically illustrates a path of a measuring signal of a pressure measurement in the delivery channel on starting up the apparatus of FIG. 1 and during its operation;

FIG. 3 graphically illustrates a path of a measuring signal of a pressure measurement in the delivery channel with a control loop, warning band and alarm band in accordance with the invention;

FIG. 4 graphically illustrates a path of a measuring signal of an optical sensor in the stuffer box on starting up the apparatus of FIG. 1 and during its operation.

Figure 1:
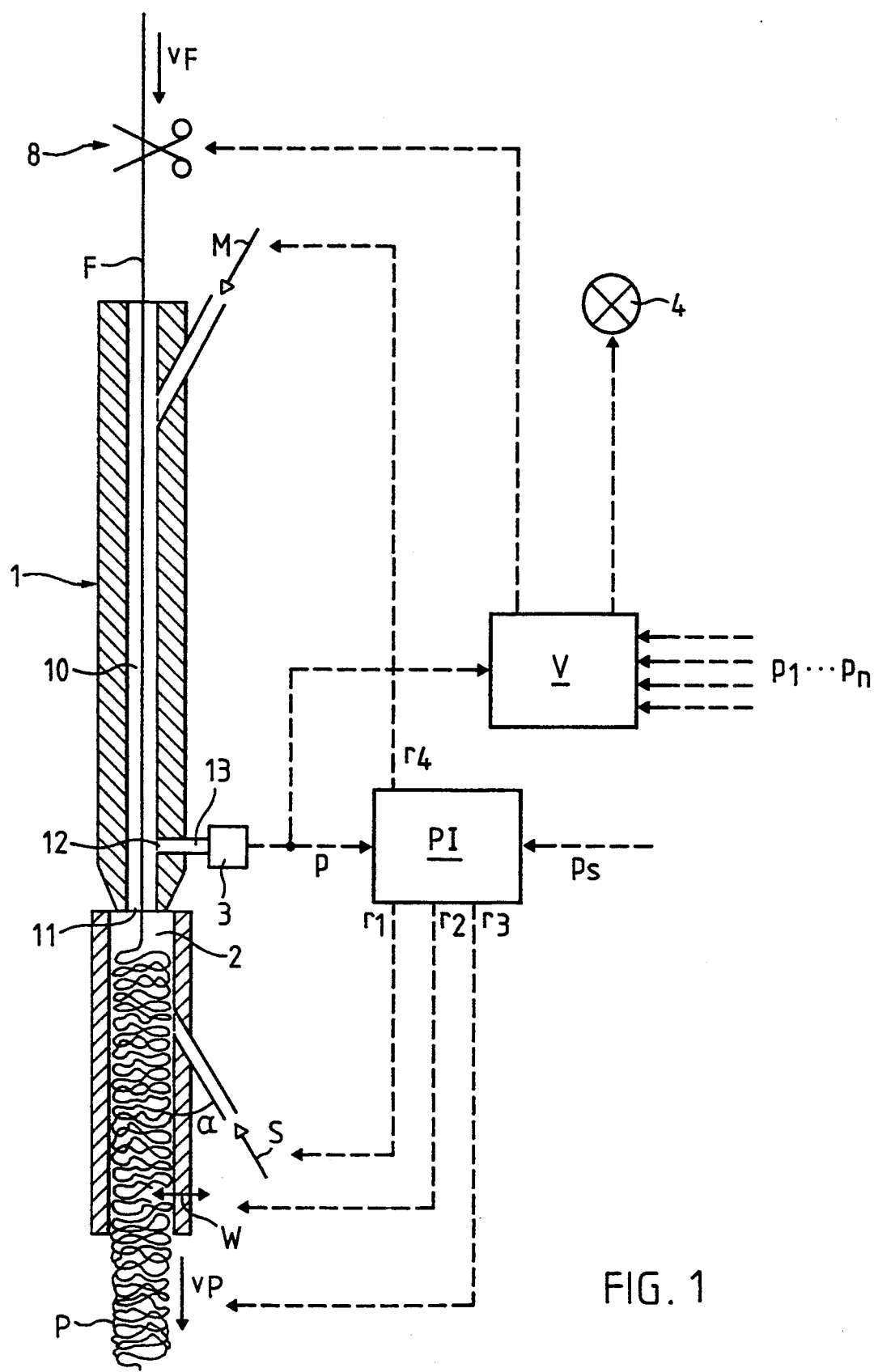

Referring to FIG. 1, the thread crimping apparatus has a texturing nozzle 1 with a delivery channel 10 and an orifice 11 and a stuffer box 2 connected thereto. A thread F is conveyed at a speed $V_F$ through the delivery channel 10 and out of the orifice 11 with the aid of a delivery medium M, which is fed under pressure into the channel 10 via a suitable inlet. The delivery medium has an elevated temperature In order to simultaneously heat the thread F. The delivery medium M is fed under pressure into the delivery channel 10 and is depressurized outside the orifice 11. The thread F is delivered by the delivery medium M through the delivery channel 10 and outside the orifice 11 strikes against a plug P, which is formed in the stuffer box 2, and conveyed on at a speed $V_P$, so as to be cooled in further stages and then loosened to a textured thread.

In the stuffer box 2, a damming back medium S can be fed under pressure against the thread at an angle ($\alpha$) to the plug movement direction. The angle ($\alpha$) is between 0 and 90°, so that the flow direction of the damming back medium has no component in the plug speed direction. The damming back medium S is more particularly used on starting up the apparatus in order to initiate plug formation by additional braking, in that the medium brakes the threads and moves against the walls of the stuffer box 2 and consequently is additionally decelerated by friction on said walls.

A sensory means is provided for monitoring at least one characteristic of plug formation in the vicinity of the orifice 11 of the delivery channel 10 in a sensory manner in order to emit a signal corresponding to a measured value of a characteristic of plug formation. As illustrated, the sensory means is in the form of a pressure measuring means which includes an opening 12 in the wall of the delivery channel to which is connected a measuring cavity 13. The measuring cavity 13 is closed with the exception of the measuring opening 12 and has a pressure measuring element 3, e.g. a piezoelectric element, enabling the pressure in the measuring cavity 13 to be measured and this corresponds to the static pressure in the delivery channel 10 in the vicinity of the measuring opening 12.

The signal from the sensory means is processed in a manner so as to maintain plug formation constant or to activate an alarm indicative of the characteristic of plug formation deviation from a preset value. In the illustrated embodiment of FIG. 1, the measured value p of the pressure measuring element 3, which corresponds to the static pressure in the delivery channel 10, is fed as a measured quantity into a proportional/integral controller PI and/or into a comparator V. With an output signal ($r_1$, $r_2$, $r_3$ or $r_4$) of the controller PI, it is possible to influence the aerodynamic braking action in the stuffer box by regulating the supply of the damming back medium ($r_1$), the mechanical friction in the stuffer box by regulating a stuffer box wall W or stuffer box geometry ($r_2$), the plug speed by regulating the speed of a plug delivery means ($r_3$) connecting onto the stuffer box, or the stuffing action by regulating the supply of the delivery medium M ($r_4$), in such a way that the dynamic pressure P corresponds to a desired value $p_s$. The desired pressure $p_s$ can be determined by tests and fed into the controller PI, or can be determined by a calibration measurement.

As indicated, the wall W of the stuffer box 2 may be adjusted in response to the processed signal $r_1$ in order to vary the cross-section of the passage through the stuffer box 2 to maintain plug formation constant. In addition to or alternatively, the flow quantity of the flowable medium fed into the stuffer box 2 may be varied in dependence upon the signal $r_2$ from the controller PI in order to maintain plug formation constant. Also, a plug delivery means (not shown) for conveying the thread plug from the stuffer box 2 at a preset speed may have the speed varied in dependence on the processed signal $r_3$ from the controller PI in order to maintain the plug formation constant.

The control elements (not shown in the drawing) for the control loop are e.g. regulating valves for the supply of the damming back medium or the delivery medium, a drive with which a brake body is moved into the stuffer box or the stuffer box is constructed in iris-like manner, or the drive of a plug delivery means, which is optionally provided and connected to the stuffer box. The regulation of the damming back medium supply is particularly appropriate in apparatuses with stuffer boxes with partly moving walls, whilst the regulation of the stuffer box wall or its geometry (e.g. the stuffer box conicity) is particularly suitable for apparatuses only having stationary stuffer box walls, the magnitudes of the necessary changes being very small (roughly 1/10 mm range). An irislike movement is particularly favorable in the case of stuffer boxes formed from individual, stationary lamellas. The regulation of the plug delivery speed is only possible if the crimping apparatus has a plug delivery means, e.g. a needle roller, connected to the stuffer box. The regulation of the delivery medium supply is not very advantageous, because it affects the thread temperature and, consequently, the crimping and can lead to quality fluctuations.

The measured value produced by the pressure measurement can also be compared with at least one measurement limit ($p_1 \ldots p_n$) in a comparator V. If limits are exceeded, it is e.g. possible to activate an alarm light 4 or to stop production by effecting a thread break for example via a cutter 8. The function of the comparator V will be described in greater detail relative to FIGS. 2, 3, and 4.

A commercially available proportional/integral controller can be used as the controller PI. An integral controller, e.g. with an alarm and stop band can be used for a combined control and comparison function. If only comparison and not control is required, then for the function of the comparator V, a circuit with a discriminator having an adjustable threshold can be used. The thresholds are set by tests. Obviously, the control and/or comparison function can also be fulfilled on a software basis.

Figure 2:
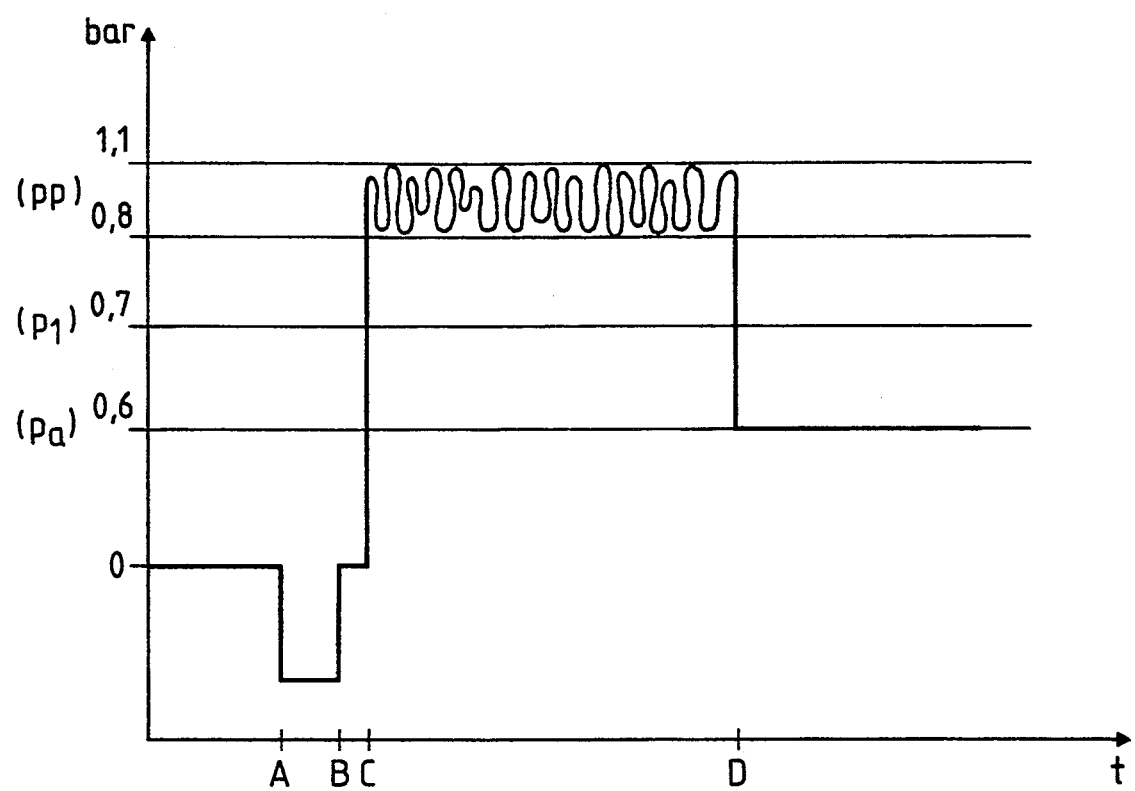
Figure 3:
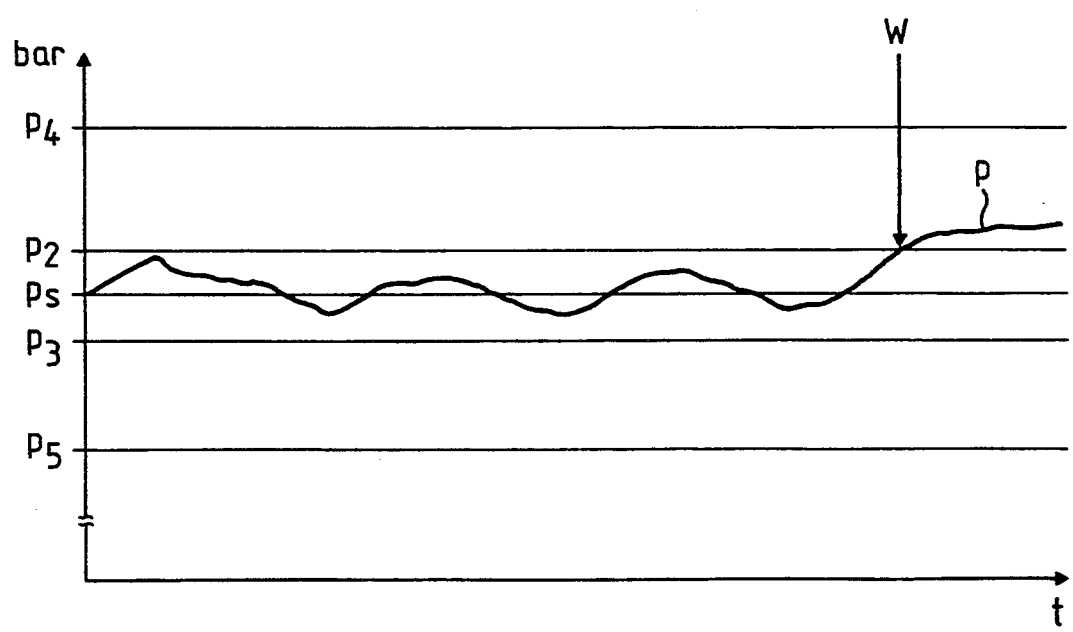
Figure 4:
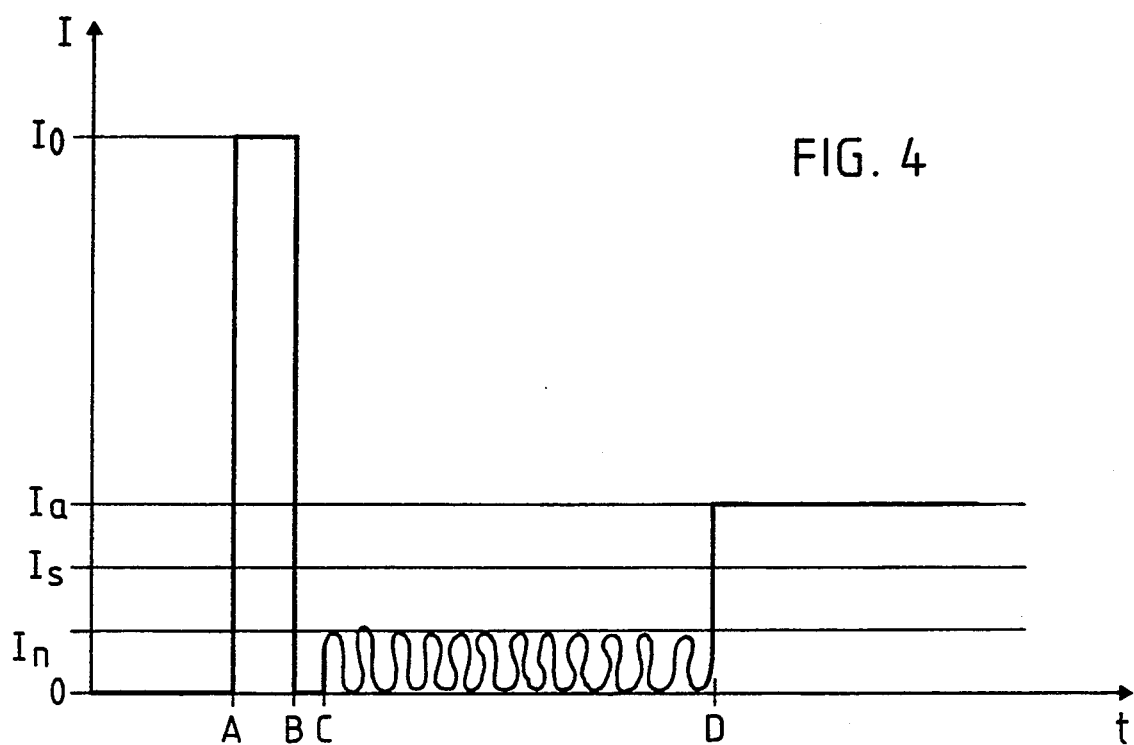

FIGS. 2, 3 and 4 show only exemplified paths of a measuring signal. On the ordinate is plotted the measuring signal or the physical quantity corresponding thereto and on the abscissa the time.

FIG. 2 shows the measuring signal path or course for an arrangement with pressure measurement in the delivery channel and evaluation of the measuring signal with a comparator. The static pressure (in bar overpressure/—under pressure) in the delivery channel and which corresponds to the measured value p (e.g. voltage) is plotted over a time axis t, the represented time contains the starting of the apparatus, stationary operation and the occurrence of a blow out.

Up to time A, no delivery medium flows through the delivery channel, the latter being closed or can be opened for preparatory work, i.e. can be subdivided along the course of the thread into two channel parts. Up to this time, the static pressure in the texturing nozzle is the same as atmospheric pressure, i.e. the measured pressure is zero. At time A, the delivery channel is closed and the delivery medium connected in to flow through the channel. The static pressure in the channel drops and remains constant during the following heating-up time. When the channel has reached the texturing temperature (time B), the delivery medium is stopped again, the channel opened and the thread drawn in. At time C, the channel is closed and immediately plug formation is initiated, e.g. by brief thread braking with the aid of the damming back medium S. As a result of the damming back of the delivery medium at the thread in the delivery channel and at the plug in the stuffer box, the static pressure in the delivery channel rises and oscillates in the case of continuous, regular operation in a pressure range corresponding to a measured value range pp. Operation can be looked upon as optimum, if the measured value range pp is as narrow as possible and remains constant over long periods of time.

At time D, a blow out occurs, i.e. the plug formation point is removed from the orifice of the delivery channel. Therefore, the damming back action of the plug becomes smaller and the measured static pressure drops, namely to a pressure corresponding to a measured value $p_a$, which in the extreme case corresponds to the static pressure in the delivery channel without the damming back action of a plug.

With a measurement in the manner of FIG. 2, in which the measured value p is followed and the plug formation observed, a measured threshold $p_1$, can be determined in such a way that irregularities in plug formation can be accepted for as long as they do not lead to measured value fluctuations, which lead to a drop below the measured threshold $p_1$. The measured threshold $p_1$ is set higher than the measured value $p_a$ for a blow out. The measured threshold $p_1$ is set sufficiently low as to have a sufficient spacing from the measured value range pp, so that, in the case of regular operation, the measured values p do not come in its range. The measured threshold $p_1$ is set sufficiently high that plug irregularities, which lead to quality losses and/or to permanent blow outs, are recognized as such.

For an apparatus in accordance with the crimping apparatus of European patent 310 890 the following pressure conditions applied. At a feed pressure of the delivery medium of 7 to 7.5 bar, the pressure range in the case of regular plug formation (measured value range pp) was between 0.8 and 1.1 bar (overpressure), the measured pressure in the case of a blow out (measured value $p_a$) was 0.6 bar, so that the threshold pressure (measured threshold $p_1$) had to be set at approximately 0.7 bar.

FIG. 3 shows an exemplified signal path for an arrangement with the measurement of the pressure in the delivery channel, with a control loop, warning band ($p_2/p_3$) and alarm band ($p_4/p_5$). During optimum operation, the regulated measured valued should be within the warning band. If the measured value is outside the warning band, but still within the alarm band, production can still take place without quality losses, but a warning W is given (warning light, protocol printout), which indicates that an inspection (cleaning) will soon be necessary. If the measured pressure rises above $p_4$ then the orifice is blocked and if the measured pressure drops below $p_5$ there is a blow out. In both cases, production must be stopped, e.g. by thread cutting.

Figure 5A:
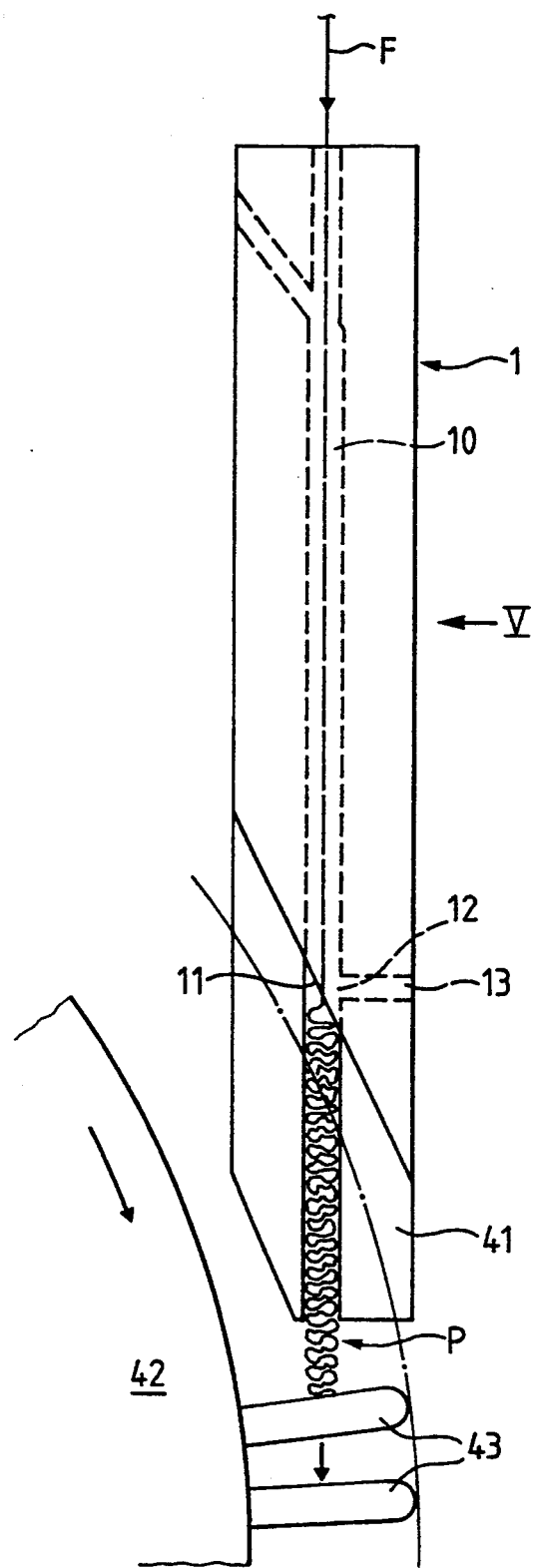
FIG. 5a illustrates a side view of a modified arrangement of a texturing nozzle and stuffer box with a measuring opening for measuring the static pressure in the delivery channel and means for optical monitoring of the stuffer box.
Figure 5B:
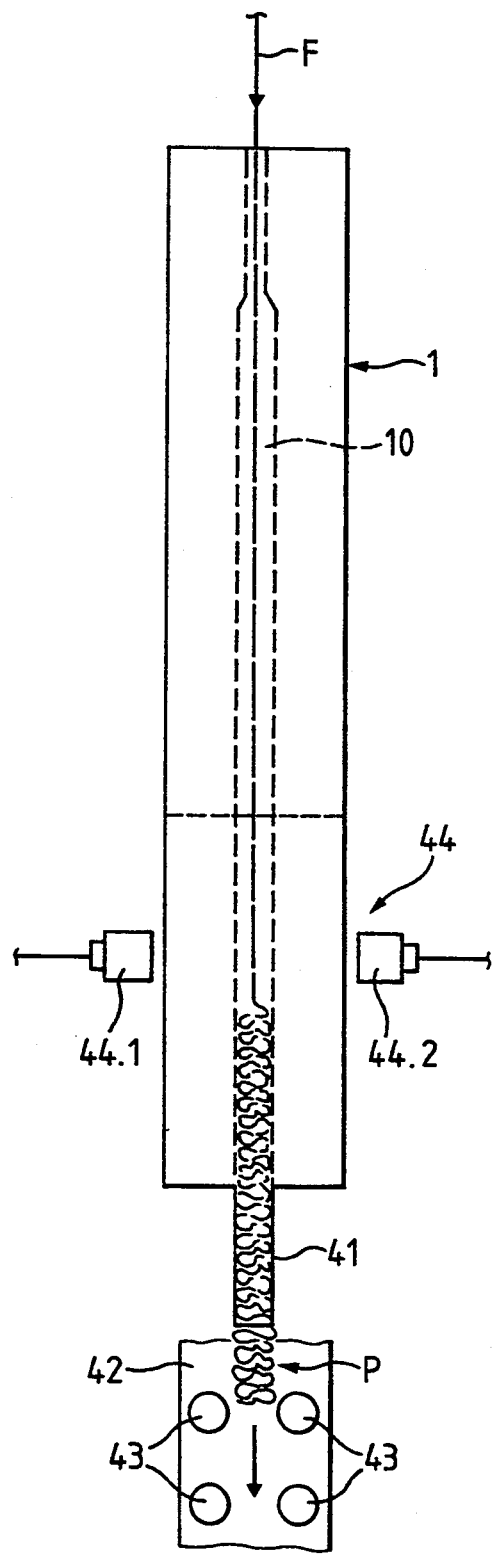
FIG. 5b illustrates a front view of a further modified.

FIG. 4 shows the path of the measuring signal I of an optical sensor in the stuffer box, plotted over the same time as in FIG. 1. The measuring signal I is e.g. the measuring signal of an optical sensor comprising a light source and a photosensitive cell, which are installed facing one another in the stuffer box. The light emitted by the light source is directed against the photosensitive cell, but is partly absorbed and scattered by the thread and/or plug. The measuring signal corresponds to the intensity of the light received by the photosensitive cell. This is high in the case of a threadless stuffer box ($I_o$), lower in the case of a substantially linearly traversing thread ($I_a$) resulting from absorption by the thread, which corresponds to a blow out, and very low in the case of a plug in the stuffer box (range $I_n$). The measured threshold $I_s$ is set at between $I_a$ and the upper limit of $I_n$. Referring to FIGS. 5a and 5b, the crimping apparatus may include a texturing nozzle 1 with shaped parts 41, which fulfill the function of the stuffer box. The texturing nozzle in FIG. 5b is rotated by 90° compared with FIG. 5a (viewing direction like arrow V in FIG. 5a). The thread F is conveyed through the delivery channel 10 and the orifice 11 and plug formation starts immediately outside the orifice. The plug P formed is conveyed away from the texturing nozzle with the aid of a plug delivery roller 42 between two rows of teeth 43.

In the apparatus according to FIG. 5a, the damming back pressure in the delivery channel is measured. The apparatus has a measuring opening 12, which leads into a measuring cavity 13. Outside the delivery channel walls, the measuring cavity 13 can assume random shapes adapted to the overall arrangement. A pressure measuring element (not shown in the drawing) is advantageously installed outside the delivery channel walls.

Figure 6:
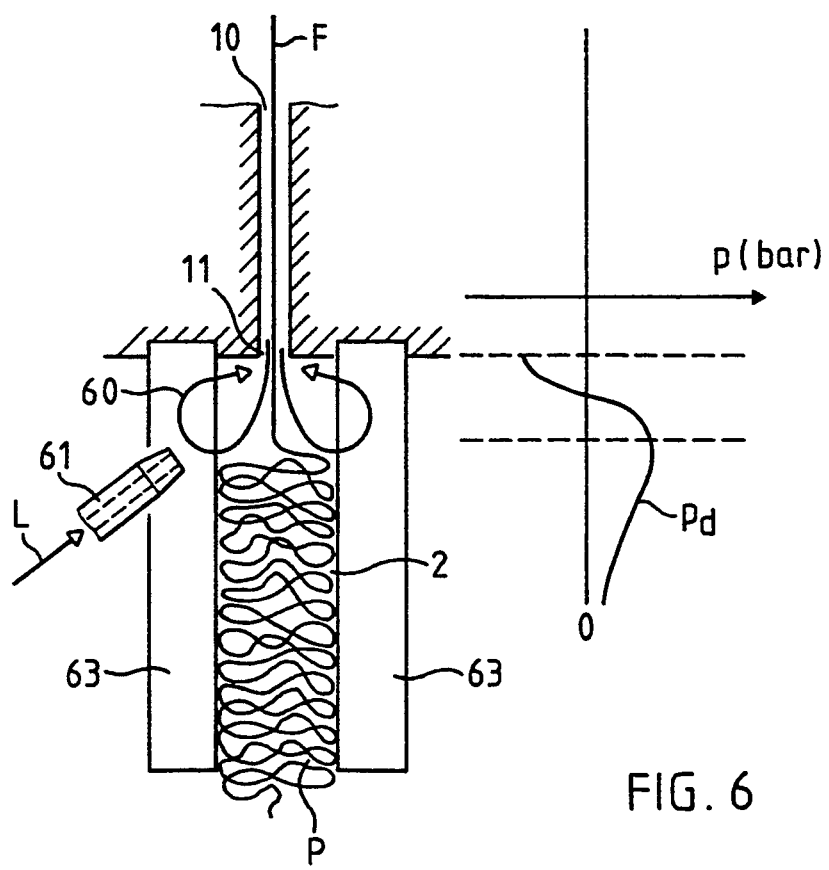
FIG. 6 illustrates a view of a texturing nozzle with a stuffer box with means for monitoring the pressure in the stuffer box.

In the apparatus according to FIG. 5b, plug formation is monitored optically. The apparatus has a light barrier 44, which can be provided alternatively to the measuring cavity and pressure measuring element. This light barrier has a light source 44.1 and a receiver 44.2, which are so fitted in facing manner on the open sides of the stuffer box, that the receiver receives the light from the light source. FIG. 6 diagrammatically shows another exemplified arrangement for the monitoring of the pressure in the vicinity of the orifice. In this embodiment, the dynamic pressure in the line for feeding the measuring air into the stuffer box is measured immediately outside the orifice.

FIG. 6 shows a delivery channel 10, in which a thread F is conveyed and a stuffer box 2 in which a plug P is formed. In the represented embodiment, the stuffer box 2 is bounded by lamellas 63 positioned radially to the plug. In the vicinity of the orifice 11, the delivery medium is depressurized between the lamellas. Measurements show that between the plug P and the orifice 11, turbulence (arrow 60) is formed, so that close to the orifice there is a flow against the thread and close to the plug a flow out of the stuffer box. The form of this turbulence is highly dependent on the geometry of the orifice and the stuffer box. If, in areas between the orifice and the start of the plug, the pressure on the stuffer box wall is measured as a function of the distance from the orifice by means of a fluidic nozzle 61, immediately outside the orifice there is an underpressure suction, which rises over a neutral zone to a pressure maximum at the start of the plug. If such a fluidic nozzle 61 is e.g. installed at the distance from the orifice where optimum plug formation commences, then from the pressure measured in the nozzle 61 information on the plug position is obtained. Such a measurement can be evaluated in the same way as the measuring signal of the sensor for the dynamic pressure in the delivery channel.

The term fluidic nozzle is used to describe a measuring nozzle through which measuring air flows at a constant level and in which the dynamic pressure is measured. Such a fluidic nozzle is particularly advantageous in the vicinity of the stuffer box, because as a result of the measuring air flow it is to a high degree self-cleaning. Advantageously, the measuring cavity or the means for monitoring the stuffer box, e.g. the light barrier, are positioned as close as possible to the orifice.

The invention thus provides a relatively simple technique embodied in a method and an apparatus for monitoring thread plug formation during the crimping of a thermoplastic yarn. The monitoring apparatus employed is relatively simple and blow outs can be readily detected.

The invention further provides a method and apparatus which is able to avoid and/or detect irregularities in plug formation in a rapid manner.

What is claimed:

1. A method for continuous crimping of a thermoplastic thread comprising the steps of conveying a travelling length of thermoplastic thread at a predetermined thread speed through a delivery channel having an orifice at one end thereof into a stuffer box with stationary walls;

passing a flow of heated delivery medium into the channel for passage out of said orifice with the thread;

braking the speed of the thread in the stuffer box to form a thread plug by moving the yarn plug along the stationary walls;

conveying the thread plug from the stuffer box at a plug speed less than said thread speed;

monitoring at least one pressure characteristic of plug formation in the vicinity of the orifice of the delivery channel to emit a signal corresponding to a measured value of said characteristic of plug formation;

and thereafter processing said signal to selectively maintain plug formation constant, to initiate a thread break or to activate an alarm indicative of said characteristic of plug formation deviating from a present value.

2. A method as set forth in claim 1 wherein said characteristic is the static pressure in the delivery channel adjacent the orifice.

3. A method as set forth in claim 1 wherein said characteristic is the pressure in the stuffer box adjacent the orifice of the delivery channel.

4. A method as set forth in claim 1 which further comprises the steps of discharging the plug from the stuffer box under a predetermined exit speed and varying said exit speed in dependence on said processed signal to maintain plug formation constant.

5. A method as set forth in claim 1 which further comprises the step of adjusting a wall part of the stuffer box in response to said processed signal to vary the cross-section of a passage through the stuffer box to maintain plug formation constant.

6. A method as set forth in claim 1 which further comprises the step of varying the quantity of the delivery medium passed into the delivery channel in response to said processed signal.

7. A method as set forth in claim 1 which further comprises the steps of establishing a threshold value for said processed signal, and activating an alarm in response to said signal passing said threshold value.

8. A method as set forth in claim 1 which further comprises the steps of establishing a threshold value for said processed signal, and interrupting conveying of the thread in the delivery channel in response to said signal passing said threshold value.

9. An apparatus for the continuous crimping of a thermoplastic thread comprising a texturing nozzle having a delivery channel for conveying travelling length of thermoplastic thread at a predetermined thread speed therethrough, an inlet into said channel for a flowable delivery medium, and an orifice at one end of said channel;

a stuffer box for receiving a thread from said orifice and forming a thread plug therein, said stuffer box having stationary walls for braking the yarn plug therealong; and sensory means for monitoring at least one pressure characteristic of plug formation in the vicinity of the orifice of the delivery channel to emit a signal corresponding to a measured value of said characteristic of plug formation.

10. An apparatus as set forth in claim 9 wherein said sensory means includes a pressure measuring element for measuring the pressure in said channel adjacent said orifice and emitting a signal corresponding thereto.

11. An apparatus as set forth in claim 9 wherein said sensory means includes a fluidic nozzle in said stuffer box adjacent said orifice for a flow of air therethrough and a pressure measuring element for measuring the pressure in said nozzle and emitting a signal corresponding thereto.

12. An apparatus for the continuous crimping of a thermoplastic thread comprising a texturing nozzle having a delivery channel for conveying a travelling length of thermoplastic thread at a predetermined thread speed therethrough, an inlet into said channel for a flowable delivery medium, and an orifice at one end of said channel;

a stuffer box for receiving a thread from said orifice and forming a thread plug therein, said stuffer box having stationary walls for braking the yarn plug therealong;

a pressure measuring element for measuring the pressure in said channel adjacent said orifice and emitting a corresponding signal in response thereto; and a proportional/integral controller for receiving said signal from said pressure measuring element and for emitting a corresponding control signal in response thereto to maintain a constant plug formation.

13. An apparatus as set forth in claim 12 which further comprises a comparator for receiving said signal from said pressure measuring element and for emitting an alarm signal in response to said received signal exceeding a preset value.

14. An apparatus as set forth in claim 12 which further comprises a plug delivery means for conveying the thread plug from said stuffer box at a preset speed and wherein said controller delivers said control signal to said plug delivery means to vary said speed of the thread plug from said stuffer box.

15. A method for continuous crimping of a thermoplastic thread comprising the steps of conveying a travelling length of thermoplastic thread at a predetermined thread speed through a delivery channel having an orifice at one end thereof into a stuffer box;

passing a flow of heated delivery medium into the channel for passage out of said orifice with the thread;

braking the speed of the thread in the stuffer box to form a thread plug;

conveying the thread plug from the stuffer box at a plug speed less than said thread speed;

monitoring the optical appearance of the thread plug at a predetermined location in the stuffer box in close proximity to said orifice as a measure of plug formation and emitting a signal corresponding thereto, and thereafter processing said signal to selectively maintain plug formation constant or to activate an alarm indicative of said characteristic of plug formation deviating from a preset value.

16. A method as set forth in claim 15 which further comprises the steps of discharging the plug from the stuffer box under a predetermined exit speed and varying said exit speed in dependence on said processed signal to maintain plug formation constant.

17. A method as set forth in claim 15 which further comprises the steps of feeding a predetermined quantity of flowable medium into the stuffer box to brake the thread therein, and varying said quantity in dependence on said processed signal to maintain plug formation constant.

18. A method as set forth in claim 15 which further comprises the step of adjusting a wall part of the stuffer box in response to said processed signal to vary the cross-section of a passage through the stuffer box to maintain plug formation constant.

19. A method as set forth in claim 15 which further comprises the step of varying the quantity of the delivery medium passed into the delivery channel in response to said processed signal.

20. A method as set forth in claim 15 which further comprises the steps of establishing a threshold value for said processed signal, and activating an alarm in response to said signal passing said threshold value.

21. A method as set forth in claim 15 which further comprises the steps of establishing a threshold value for said processed signal, and interrupting conveying of the thread in the delivery channel in response to said signal passing said threshold value.

22. A method for continuous crimping of a thermoplastic thread comprising the steps of
conveying a travelling length of thermoplastic thread at a predetermined thread speed through a delivery channel having an orifice at one end thereof into a stuffer box;
passing a flow of heated delivery medium into the channel for passage out of said orifice with the thread;
braking the speed of the thread in the stuffer box to form a thread plug;
conveying the thread plug from the stuffer box at a plug speed less than said thread speed;
monitoring at least one pressure characteristic of plug formation in the vicinity of the orifice of the delivery channel to emit a signal corresponding a measured value of said characteristic of plug formation;
thereafter processing said signal to selectively maintain plug formation constant or to activate an alarm indicative of said characteristic of plug formation deviating from a preset value;
feeding a predetermined quantity of flowable medium into the stuffer box to brake the thread therein; and
varying said quantity of flowable medium in dependence on said processed signal to maintain plug formation constant.

23. An apparatus for the continuous crimping of a thermoplastic thread comprising
a texturing nozzle having a delivery channel for conveying a travelling length of thermoplastic thread at a predetermined thread speed therethrough, an inlet into said channel for a flowable delivery medium, and an orifice at one end of said channel;
a stuffer box for receiving a thread from said orifice and forming a thread plug therein; and
an optical sensor in said stuffer box and in close proximity to said orifice for monitoring the formation of a thread plug thereat and emitting a signal corresponding thereto.

24. An apparatus for the continuous crimping of a thermoplastic thread comprising
a texturing nozzle having a delivery channel for conveying a travelling length of thermoplastic thread at a predetermined thread speed therethrough, an inlet into said channel for a flowable delivery medium, and an orifice at one end of said channel;
a stuffer box for receiving a thread from said orifice and forming a thread plug therein;
a pressure measuring element for measuring the pressure in said channel adjacent said orifice and emitting a corresponding signal in response thereto;
means for feeding a predetermined quantity of a flowable medium into said stuffer box to brake the thread plug; and
a proportional/integral controller for receiving said signal from said pressure measuring element and for emitting a corresponding control signal in response thereto to said means to vary the braking of the thread plug in said stuffer box to maintain a constant plug formation.

* * * * *

UNITED STATES PATENT AND TRADEMARK OFFICE
CERTIFICATE OF CORRECTION

PATENT NO. : 5,351,374
DATED : October 4, 1994
INVENTOR(S) : Werner Nabulon, et al It is certified that error appears in the above-indentified patent and that said Letters Patent is hereby corrected as shown below:

```
Column 1, line 50 change "Lateral" to -lateral-
Column 4, line 50 after "modified" insert -arrangement-
   Line 62 change "In" to -in-
Column 5, line 11 change "threads" to -thread-
Column 7, line 43 change "valued" to -value-
Column 9, line 65 before "travelling" insert -a-
```

Signed and Sealed this

Thirty-first Day of January, 1995

Attest:

BRUCE LEHMAN

Attesting Officer

Commissioner of Patents and Trademarks